United States Patent
Hasegawa

(10) Patent No.: US 10,085,719 B2
(45) Date of Patent: Oct. 2, 2018

(54) CAPACITIVE MICROMACHINED ULTRASONIC TRANSDUCER AND METHOD FOR PRODUCING THE SAME

(71) Applicant: CANON KABUSHIKI KAISHA, Tokyo (JP)

(72) Inventor: Yoshihiro Hasegawa, Tama (JP)

(73) Assignee: Canon Kabushiki Kaisha, Tokyo (JP)

( * ) Notice: Subject to any disclaimer, the term of this patent is extended or adjusted under 35 U.S.C. 154(b) by 677 days.

(21) Appl. No.: 14/738,298

(22) Filed: Jun. 12, 2015

(65) Prior Publication Data

US 2015/0366539 A1    Dec. 24, 2015

(30) Foreign Application Priority Data

Jun. 18, 2014 (JP) .................. 2014-125834

(51) Int. Cl.
| | |
|---|---|
| *A61B 8/00* | (2006.01) |
| *A61B 5/00* | (2006.01) |
| *C23C 16/34* | (2006.01) |
| *C23C 16/40* | (2006.01) |
| *C23C 16/513* | (2006.01) |
| *B06B 1/02* | (2006.01) |

(52) U.S. Cl.
CPC .......... *A61B 8/4483* (2013.01); *A61B 5/0095* (2013.01); *B06B 1/0292* (2013.01)

(58) Field of Classification Search
CPC .... B06B 1/0292; A61B 8/4483; A61B 5/0095
See application file for complete search history.

(56) References Cited

U.S. PATENT DOCUMENTS

| | | | |
|---|---|---|---|
| 5,894,452 A | 4/1999 | Ladabaum | |
| 8,890,076 B2* | 11/2014 | Dirksen | A61B 1/05 250/349 |
| 2008/0194053 A1* | 8/2008 | Huang | B06B 1/0292 438/53 |
| 2009/0103083 A1* | 4/2009 | Kremeyer | G01N 21/1702 356/317 |
| 2012/0250006 A1* | 10/2012 | Kremeyer | G01N 21/1702 356/72 |
| 2015/0366539 A1* | 12/2015 | Hasegawa | B06B 1/0292 600/459 |

FOREIGN PATENT DOCUMENTS

| | | |
|---|---|---|
| JP | 2006319712 A | 11/2006 |
| JP | 2013065983 A | 4/2013 |
| JP | 2013126070 A | 6/2013 |

* cited by examiner

*Primary Examiner* — Daniel Pihulic
(74) *Attorney, Agent, or Firm* — Canon USA, Inc., IP Division

(57) ABSTRACT

In a method for producing a capacitive micromachined ultrasonic transducer having a cell of a structure having a first electrode and a vibration membrane containing a second electrode provided with a cavity interposed between the first electrode and the second electrode, a first sacrificial layer is formed on the first electrode. A second sacrificial layer is formed on a portion corresponding to a part of a cavity is formed on the first sacrificial layer, and then an insulating layer configuring a part of the vibration membrane is formed on the second sacrificial layer. The second sacrificial layer is removed by etching through an opening formed in the insulating layer, and then a part of the first sacrificial layer is removed.

20 Claims, 8 Drawing Sheets

CAPACITIVE MICROMACHINED ULTRASONIC TRANSDUCER AND METHOD FOR PRODUCING THE SAME

BACKGROUND OF THE INVENTION

Field of the Invention

The present invention relates to a capacitive micromachined ultrasonic transducer to be used as an ultrasonic transducer and the like, a method for producing the same, a subject information acquisition device, and the like.

Description of the Related Art

In recent years, various micromachined elements processed with micrometer order accuracy has been developed with the development of micromachining techniques. Using such techniques, a capacitive micromachined ultrasonic transducer (CMUT) has been actively developed. The CMUT is an ultrasonic device which vibrates a lightweight vibration membrane to transmit and receive acoustic waves, such as ultrasonic waves, and one having excellent broadband characteristics both in liquid and in the air is easily obtained. Therefore, when the CMUT is medically utilized, diagnosis whose accuracy is higher than that of ultrasonic devices containing piezoelectric elements used heretofore can be achieved. Thus, the CMUT has drawn attention as a substitute therefor. Sound waves, ultrasonic waves, photoacoustic waves, and the like are referred to as acoustic waves, which are represented by ultrasonic waves in some cases in this specification.

The capacitive micromachined ultrasonic transducer has one or more cell structures. The cell structure is configured from a first electrode disposed on a substrate of Si or the like, a second electrode disposed facing the first electrode, a cavity (gap) formed between the first electrode and the second electrode, a vibration membrane which contains the second electrode and is formed on the cavity, and a vibration membrane support portion. As one of methods for producing the capacitive micromachined ultrasonic transducer, a surface micromachining production method is mentioned which includes depositing a material on a substrate of Si or the like, and then forming the same. The formation of a cavity portion in this production method is performed by sacrificial layer etching. Specifically, a sacrificial layer is patterned in a portion serving as a cavity while leaving the size of the cavity which determines the characteristics of the transducer, and then a membrane configuring at least one part of the vibration membrane is deposited thereon. Thereafter, the sacrificial layer is removed from an etching hole (opening) which is formed in a part of the membrane and communicates with the sacrificial layer, whereby the cavity is formed. Since the capacitive micromachined ultrasonic transducer is used in a solvent in water, in oil, and the like in some cases, the etching hole provided in order to etch the sacrificial layer is sealed by depositing a film.

In the process of depositing the membrane on a sacrificial layer material, the membrane on the sacrificial layer material serves as a vibration membrane which vibrates in order to transmit and receive ultrasonic waves, and the vibration membrane in end portions of the sacrificial layer material serves as a support portion which supports the vibration membrane as a rigid body. The characteristics of the capacitive micromachined ultrasonic transducer thus produced are mainly determined based on the diameter of the cavity of the cell structure, the thickness of the vibration membrane formed on the cavity, and the height (thickness) of the cavity. In usual, when the vibration membrane vibrates, the vibration membrane is used under the conditions where the vibration membrane does not contact the bottom face of the cavity. Therefore, in order to increase the displacement of the vibration membrane for the purpose of increasing the transmission sound pressure, the height of the cavity needs to be increased. However, when the height of the cavity is increased, the thickness of the membrane support portion needs to be sufficiently secured in steps in the end portions of the sacrificial layer material patterned into the cavity shape. Therefore, the membrane needs to be formed with a film thickness which can sufficiently cover (i.e., which realizes a sufficient coverage) the sacrificial layer thickness (i.e., cavity height). The thickness is dependent also on a film forming device and needs to be at least 1 to 2 times the sacrificial layer thickness.

In view of the description above, the method including patterning a sacrificial layer in such a manner as to leave the entire shape of a cavity, forming a vibration membrane, and then removing the sacrificial layer to form a cavity has posed the following problems. More specifically, when the thickness of the sacrificial layer is increased in order to increase the transmission sound pressure, for example, for controlling the characteristics of a capacitive micromachined ultrasonic transducer, the thickness of the membrane needs to be increased in connection with the increase in the thickness of the sacrificial layer. More specifically, a large thickness of the sacrificial layer and a small thinness of the membrane have a trade-off relationship, and therefore it is not easy to increase the thickness of the sacrificial layer and reduce the thickness of the membrane.

In a capacitive micromachined ultrasonic transducer described in U.S. Pat. No. 5,894,452, a sacrificial layer is deposited on a flat substrate of Si or the like, a vibration membrane is formed thereon, and then the sacrificial layer is isotropically removed from an etching hole which opens into the center of the vibration membrane serving as the cell structure to form a cavity. According to this method, since the sacrificial layer is not patterned into a cavity shape beforehand, a step portion does not arise regardless of the thickness of the sacrificial layer. Therefore, the thickness of the membrane can be set regardless of the thickness of the sacrificial layer. However, the cavity diameter which determines the characteristics of the capacitive micromachined ultrasonic transducer is determined based on the control of the etching time of the sacrificial layer material to be removed from the etching hole which opens into the membrane, and therefore it is hard to say that it is easy to correctly control the cavity diameter. Moreover, there is a possibility that a performance variation due to a size variation of the cavity diameter in devices may arise.

As described above, according to the former production method, when the cavity height is increased, the thickness of the vibration membrane needs to be increased by a certain level or more in connection with the increase in the cavity height, which reduces the degree of freedom in design of the cell structure.

SUMMARY OF THE INVENTION

According to an aspect of the present invention, a method for producing a capacitive micromachined ultrasonic transducer having a cell of a structure having a first electrode and a vibration membrane containing a second electrode provided with a cavity interposed between the first electrode and the second electrode according to an aspect of the present invention includes the following processes: a process of forming the first electrode; a process of forming a first sacrificial layer on the first electrode; a process of forming a second sacrificial layer on a portion corresponding to a part of the cavity on the first sacrificial layer; a process of forming an insulating layer configuring at least a part of the vibration membrane on the second sacrificial layer; a process of removing the second sacrificial layer by etching through an opening formed in the insulating layer; and a process of removing a part of the first sacrificial layer after removing the second sacrificial layer.

According to another aspect of the present invention, a capacitive micromachined ultrasonic transducer has a cell of a structure having a first electrode and a vibration membrane containing a second electrode provided with a cavity interposed between the first electrode and the second electrode. A support portion which supports the vibration membrane of the cell in such a manner as to be able to vibrate is provided, and the support portion includes a sacrificial layer left behind when forming the cavity by sacrificial layer etching.

Further features of the present invention will become apparent from the following description of exemplary embodiments with reference to the attached drawings.

DESCRIPTION OF THE EMBODIMENTS

The present invention realizes a technique in which, even in the case of a capacitive micromachined ultrasonic transducer which is configured so that the cavity height is large, the diameter of a cavity can be correctly controlled and the thickness of a vibration membrane can be reduced, so that the degree of freedom in design is increased. To that end, a first sacrificial layer is formed on a first electrode, a second sacrificial layer is formed on the first sacrificial layer, and then the second sacrificial layer is patterned in such a manner as to leave a shape corresponding to a part of the cavity. Then, the second sacrificial layer is removed by etching through an opening formed in an insulating layer formed on the second sacrificial layer, and then the first sacrificial layer is removed, whereby the cavity is formed.

Hereinafter, Embodiment and Examples of the present invention are described with reference to the drawings.

Embodiment

Figure 1:
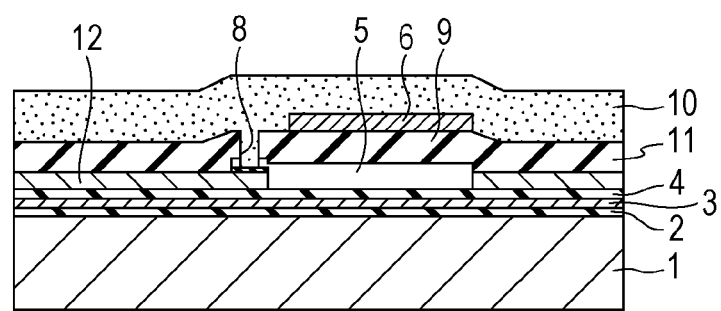
FIG. 1 is a cross sectional view of one embodiment of a capacitive micromachined ultrasonic transducer according to an aspect of the present invention.

FIG. 1 is a cross sectional view of a capacitive micromachined ultrasonic transducer according to one embodiment. Although FIG. 1 illustrates only one cell structure, the number of the cell structures in the capacitive micromachined ultrasonic transducer is not limited. In that case, any cell arrangement may be acceptable. As the shape of the vibration membrane and a membrane, any shape, such as a circular shape, a rectangular shape, and a hexagonal shape, may be acceptable.

The capacitive micromachined ultrasonic transducer of this embodiment is described. The capacitive micromachined ultrasonic transducer has a substrate 1 of Si or the like, an insulating layer 2 formed on the substrate 1, and a first electrode 3 formed on the insulating layer 2. On the first electrode 3, a vibration membrane containing a second electrode 6 and a sealing film 10 which seals a membrane 9 on a cavity 5 and the cavity 5 is formed through the cavity 5 and the membrane 9 is supported by a membrane support portion 11. The entire vibration membrane is supported by a support portion containing a remaining portion of the first sacrificial layer 12 described later, the membrane support portion 11, and end portions of the sealing film 10. Herein, the substrate 1 can also serve as the first electrode 3. When the substrate 1 is an insulator, such as a glass substrate, the insulating layer 2 may not be provided.

In FIG. 1, although the second electrode 6 is formed on the membrane 9, the second electrode 6 may be disposed on the sealing film 10 on the cavity 5. Moreover, a voltage application means (not illustrated) which applies a voltage between the first electrode 3 and the second electrode 6 is provided. By applying an alternating voltage between the first electrode 3 and the second electrode 6, the vibration membrane can be vibrated to transmit ultrasonic waves. Due to the fact that the vibration membrane receives the ultrasonic waves and vibrates in the state where the voltage is applied, the ultrasonic waves can be received as current signals.

For the formation of the cavity 5 of the capacitive micromachined ultrasonic transducer, a production method employing sacrificial layer etching which includes disposing a sacrificial layer beforehand on a portion serving as the cavity 5, and then removing the sacrificial layer from an etching hole 8 which opens into a part of the membrane 9 to thereby form the cavity 5 is used. Herein, the sacrificial layer in the production method of this embodiment is formed from the first sacrificial layer 12 formed on the first electrode 3 and a second sacrificial layer 13 formed on the first sacrificial layer 12 (FIG. 3E, etc.). The second sacrificial layer 13 is patterned beforehand in such a manner as to leave a shape serving as a part (upper portion) of the cavity 5. After forming the membrane 9 containing the membrane support portion 11 on the first sacrificial layer 12 and the patterned second sacrificial layer 13, the etching hole 8 for removing the sacrificial layer is formed in a part of the membrane 9.

Next, the second sacrificial layer 13 is removed from the etching hole 8. The diameter of the cavity 5 is determined based on the shape of the second sacrificial layer 13 patterned beforehand at this time. Next, the first sacrificial layer 12 is removed from the etching hole 8. Only a part of the first sacrificial layer 12 can be selectively removed by appropriately selecting materials of the membrane 9 and the like. Since a lower portion of the upper portion of the cavity 5 formed by removing the second sacrificial layer 13 is etched, the diameter of the lower portion of the cavity 5 formed by removing a part of the first sacrificial layer 12 is determined based on the diameter of the second sacrificial layer 13. More specifically, the diameter of the entire cavity 5 is substantially determined based on the diameter of the second sacrificial layer 13. On the other hand, the height of the cavity 5 is determined based on the total of the height of the first sacrificial layer 12 and the height of the second sacrificial layer 13. The thickness of the membrane 9 which realizes sufficient coverage in a step in end portions of the second sacrificial layer material is determined based on the thickness of the second sacrificial layer 13. Therefore, the thickness of the membrane 9 can be determined regardless of the height of the cavity 5 which is the total of the first sacrificial layer 12 and the second sacrificial layer 13.

After forming the cavity 5 by the sacrificial layer etching, the sealing film 10 is deposited on the etching hole 8 used for the sacrificial layer etching to seal the etching hole 8. As described above, the vibration membrane contains, in addition to the second electrode 6, the sealing film 10 which seals the membrane 9 formed on the cavity 5 and the etching hole 8.

Among materials configuring the capacitive micromachined ultrasonic transducer, particularly a material forming the cavity has desirably a low surface roughness in such a manner that the vibration membrane does not contact the bottom face of the cavity when the vibration membrane vibrates.

As described above, according to the method for producing a capacitive micromachined ultrasonic transducer, the cavity 5 is formed by the sacrificial layer etching. Therefore, in the sacrificial layer etching process, the etching selectivity of sacrificial layer materials to materials configuring the vibration membrane and the electrodes needs to be high. In the process of removing the second sacrificial layer 13, the membrane 9 and the first sacrificial layer 12 are exposed to an etching solution. Therefore, a material of the second sacrificial layer 13 needs to have high etching selectivity to the first sacrificial layer 12 and the membrane 9. More specifically, it is required for the etching rate of the second sacrificial layer 13 to be sufficiently higher than the etching rate of the first sacrificial layer 12 and the membrane 9. In the process of removing the first sacrificial layer 12, the membrane 9 and the first electrode 3 are exposed to an etching solution. Therefore, a material of the first sacrificial layer 12 needs to have high etching selectivity to the membrane 9 and the first electrode 3. For a material of the first electrode 3, materials, such as titanium, aluminum, molybdenum, and tungsten, can be used. In particular, titanium and tungsten are desirable because a change in the roughness due to the influence of heat applied during the process is small.

An insulating film configuring the membrane 9 and the sealing film 10 of the vibration membrane is described. As a material thereof, a silicon oxide film, a silicon nitride film, and the like can be used. In particular, a silicon nitride film formed by a plasma enhanced-chemical vapor deposition (PE-CVD) device can be formed at a low temperature 400° C. or less, and therefore the influence of heat on the other constituent materials can be made low. Moreover, since the film formation can be performed while controlling the tensile stress to low tensile stress of 300 MPa or less, large deformation of the membrane due to residual stress of the membrane can be prevented. The sealing film 10 is demanded to have a function of sealing the cavity 5 on the etching hole 8 in addition to the function of configuring the vibration membrane. It is desirable for a sealing material of the etching hole 8 to have high coverage properties and not to enter a lower portion of the membrane 9 from the etching hole 8 in order to be deposited on the etching hole 8 for sealing. This is because, when the sealing film material enters the cavity 5 in the lower portion of the membrane 9, the height of the cavity 5 relating to the performance changes. For example, in a silicon nitride film formed by low pressure-chemical vapor deposition (LP-CVD), the membrane is likely to enter the inside of the cavity, and therefore the height of the cavity 5 changes. Also as a material which satisfies such conditions, a silicon nitride film formed by PE-CVD is desirable. Since the second electrode 6 is a material configuring a part of the vibration membrane, a material thereof needs to have relatively small stress. For example, titanium, aluminum, and the like can be used.

In view of the conditions described above, chromium, titanium, and aluminum can be used for the material of the second sacrificial layer 13. For the material of the first sacrificial layer 12, amorphous silicon can be used. In particular, it is desirable to use chromium for the material of the second sacrificial layer 13, use amorphous silicon for the material of the first sacrificial layer 12, and aluminum for the first electrode 3. In the configuration, when a chromium etching solution containing ceric ammonium nitrate and nitric acid is used as an etchant for the second sacrificial layer 13, the following effects are obtained. More specifically, very high etching selectivity can be taken to the aluminum of the first electrode 3, the silicon nitride film of the membrane 9, and the amorphous silicon of the first sacrificial layer 12, which are exposed to the etchant when etching the second sacrificial layer 13. Therefore, the cavity diameter can be determined based on the patterning accuracy of chromium of the second sacrificial layer 13.

In the case where amorphous silicon is used for the first sacrificial layer 12, when a gas containing $XeF_2$ is used as the etchant for the first sacrificial layer 12, the following effects are obtained. More specifically, since very high etching selectivity can be taken to the silicon nitride film of the membrane 9 and the aluminum of the first electrode 3 which are exposed to the etchant when etching the first sacrificial layer 12, only the first sacrificial layer 12 can be selectively etched. Therefore, the height of the cavity 5 can be increased by the first sacrificial layer 12 while maintaining the diameter of the cavity formed with the second sacrificial layer 13.

Figure 2:
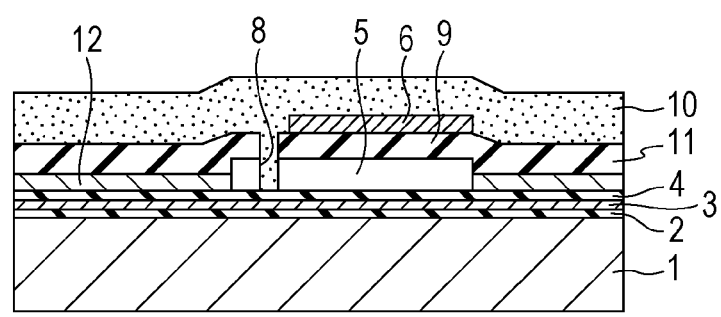
FIG. 2 is a cross sectional view of one example of the capacitive micromachined ultrasonic transducer according to an aspect of the present invention.

Moreover, a configuration in which an insulating film 4 containing a silicon oxide film or a silicon nitride film is formed on the first electrode 3 can also be taken (FIG. 2). When such a configuration is taken, when etching the first sacrificial layer 12, a material to be exposed to an etchant is not the first electrode 3 but the insulating film 4. The etching selectivity of the silicon oxide film or the silicon nitride film which is the material of the insulating film 4 to the etchant for the amorphous silicon which is the material of the first sacrificial layer 12 is very high. Therefore, the material of the first electrode 3 can be selected regardless of the selectivity of the etchant which etches the first sacrificial layer 12, and titanium, tungsten, and the like having high resistance to the heat process can be selected.

The characteristics of the capacitive micromachined ultrasonic transducer are mainly determined based on the cavity diameter, the cavity height, and the thickness of the membrane on the cavity. Since the diameter of the cavity at this time is a diameter of the membrane which can vibrate, the diameter of the cavity is determined based on the shape of the patterned second sacrificial layer. In the method for producing the capacitive micromachined ultrasonic transducer of this embodiment, the cavity 5 is produced using a two-layer sacrificial layer containing the first sacrificial layer 12 and the second sacrificial layer 13. At this time, the second sacrificial layer 13 is patterned beforehand in such a manner as to leave a portion serving as a part of the cavity 5. The vibration membrane is formed on the first sacrificial layer 12 and the second sacrificial layer 13, the second sacrificial layer 13 is removed from an opening formed in the vibration membrane, and then the first sacrificial layer 12 is removed. In the capacitive micromachined ultrasonic transducer produced with such a configuration, the diameter of the cavity 5 is determined based on the second sacrificial layer 13 patterned beforehand and the height of the cavity 5 is determined based on the total of the thickness of the second sacrificial layer 13 and the thickness of the first sacrificial layer 12. The thickness of the membrane 9 to be formed on the second sacrificial layer 13 depends on not the height of the cavity 5 but the height of the second sacrificial layer 13. Therefore, in the configuration in which the cavity diameter is correctly controlled by the second sacrificial layer 13, a configuration in which the height of the cavity 5 can be increased and the thickness of the membrane 9 does not depend on the height of the cavity 5 can be realized, so that the degree of freedom in design improves. More specifically, according to the present production method, by reducing the thickness of the second sacrificial layer which determines the cavity diameter and the thickness of the membrane to be relatively small and increasing the thickness of the first sacrificial layer which relates to the cavity height to be relatively large, for example, the cavity diameter can be correctly controlled and the cavity height can be increased. The thickness of the membrane at this time can be determined based on the thickness of the second sacrificial layer which can be formed with a relatively small thickness regardless of the height of the entire cavity.

On the other hand, in a former production method including forming a vibration membrane on a sacrificial layer patterned beforehand, and then removing the sacrificial layer to form the entire cavity, the cavity diameter can be correctly controlled but, in order to increase the cavity height, the thickness of the sacrificial layer needs to be increased. The thickness of the membrane needs to be large in connection with the increase in the thickness of the sacrificial layer.

In the etching of the first sacrificial layer, it is necessary to perform the etching while controlling the etching time to a certain degree. In order to eliminate such necessity, a production method including forming a first sacrificial layer on the entire region, performing etching in such a manner as to leave a portion serving as a lower portion of a cavity, and then embedding a material which is hard to be etched into the removal portion can also be employed. Or, a production method including first forming a material which is hard to be etched on the entire region, etching a portion serving as a lower portion of a cavity, and then embedding a material of a first sacrificial layer into the removal portion can also be employed. Thus, the necessity of controlling the etching time is substantially eliminated in the etching of the first sacrificial layer.

Example 1

FIG. 2 shows Example 1 of the capacitive micromachined ultrasonic transducer according to an aspect of the present invention. Although this example of FIG. 2 also illustrates a capacitive micromachined ultrasonic transducer having only one cell structure, the number of the cell structures is not limited. Moreover, although a view in which one etching hole is provided in one cell structure is illustrated, the number of the etching holes is not limited.

The capacitive micromachined ultrasonic transducer of this example has the silicon substrate 1 having a thickness of 300 μm, the insulating layer 2 containing a thermal oxidation film formed on the substrate 1, the first electrode 3 of tungsten formed on the insulating layer 2, and the insulating film 4 containing a silicon oxide film formed on the first electrode 3. Then, a part of the first sacrificial layer 12 and the second sacrificial layer 13 are removed from the etching hole 8, whereby the cavity 5 is formed. The vibration membrane containing the second electrode 6, the membrane 9, and the sealing film 10 is supported by the membrane support portion 11 and the like through the cavity 5, and the etching hole 8 is sealed by the sealing film 10. Moreover, a voltage application means (not illustrated) which applies a voltage between the first electrode 3 and the second electrode 6 is provided.

A method for producing the capacitive micromachined ultrasonic transducer according to this example is described with reference to the process flow of FIGS. 3A to 3F and FIGS. 3G to 3K.

Figure 3A:
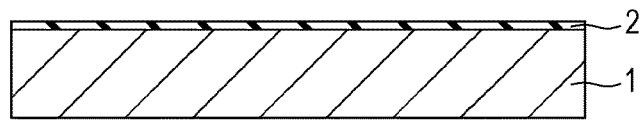
FIGS. 3A to 3F are cross sectional views of one example of a production method according to an aspect of the present invention.
Figure 3B:
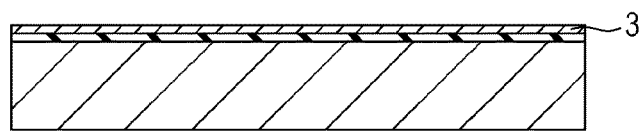
Figure 3C:
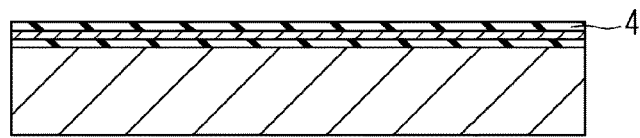
Figure 3D:
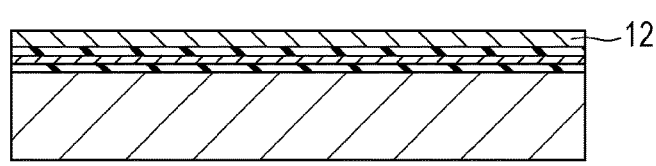
Figure 3E:
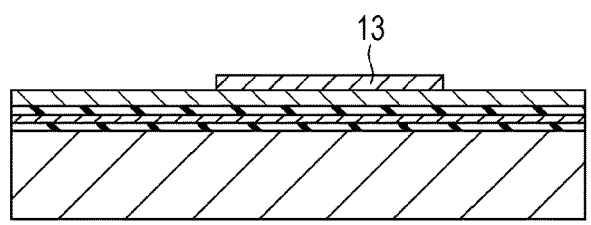
Figure 3F:
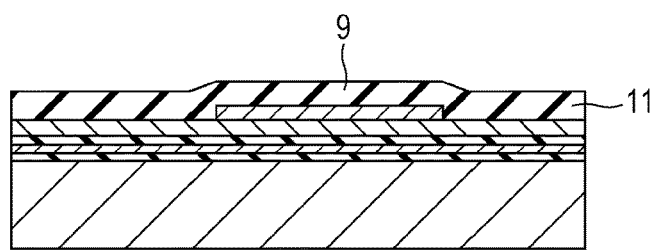

The insulating layer 2 containing a thermal oxidation film, the first electrode 3 containing tungsten, and the insulating film 4 containing a silicon oxide film are formed on the silicon substrate 1 (FIGS. 3A to 3C). Next, a 200 nm thick amorphous silicon film serving as the first sacrificial layer 12 is formed on the insulating film 4 with a PE-CVD device (FIG. 3D). Next, a 100 nm thick chromium is formed into a film as the second sacrificial layer 13 with an EB evaporator. The chromium is etched using an etchant containing ceric ammonium nitrate and nitric acid using a photolithographic technique, and then the second sacrificial layer 13 is patterned in such a manner as to leave the shape of the cavity 5 (shape of the upper portion of the entire cavity 5) (FIG. 3E). Then, a 150 nm thick silicon nitride film serving as the membrane 9 is formed with a PE-CVD device on the first sacrificial layer 12 and the patterned second sacrificial layer 13 (FIG. 3F). At this time, the silicon nitride film on the first sacrificial layer 12 serves as the support portion 11 of the membrane 9 and the silicon nitride film on the second sacrificial layer 13 serves as the membrane 9. The thickness of the membrane 9 may be a thickness which can sufficiently cover the thickness of the second sacrificial layer 13 (i.e., sufficient coverage can be achieved in corner portions of the second sacrificial layer 13).

Figure 3G:
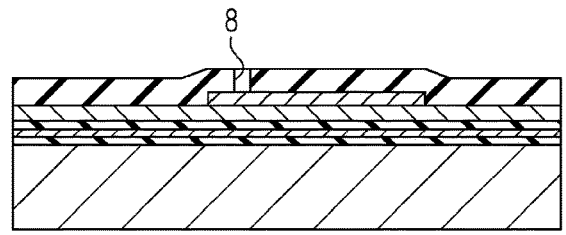
FIGS. 3G to 3K are cross sectional views of one example of the production method according to an aspect of the present invention.
Figure 3H:
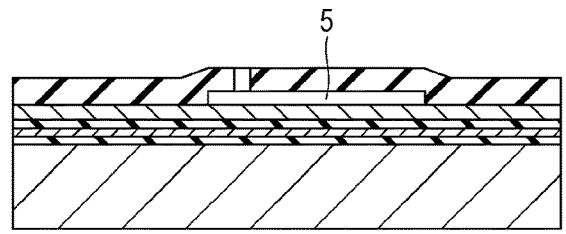
Figure 3I:
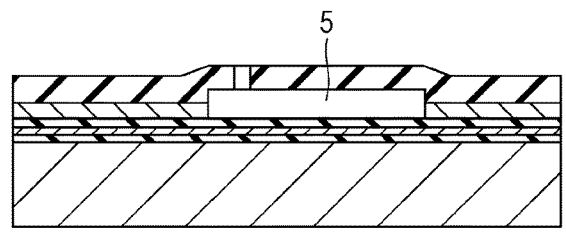
Figure 3J:
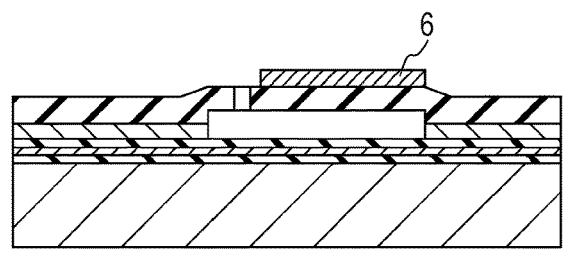
Figure 3K:
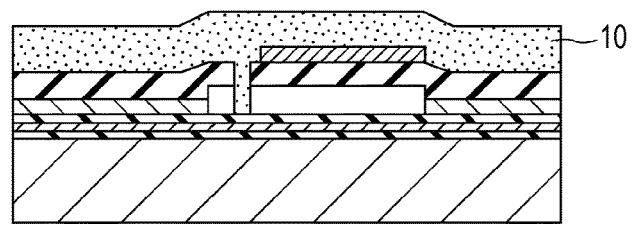

Next, the etching hole 8 for removing the sacrificial layer is made to open into a part of the membrane 9 (FIG. 3G). Then, by performing immersion in a chromium etchant containing ceric ammonium nitrate and nitric acid, the second sacrificial layer 13 is etched through the etching hole 8 to form a part of the cavity 5 (FIG. 3H). The diameter of the cavity 5 at this time is determined based on the diameter of the chromium of the second sacrificial layer 13. Next, from the same etching hole 8 as the opening used for the etching of the second sacrificial layer 13, $XeF_2$ gas which is an etchant for the first sacrificial layer 12 is introduced, so that the first sacrificial layer 12 is etched (FIG. 3I). In this process, the cavity 5 produced by etching the second sacrificial layer 13 is formed on the entire cavity having the total height of the first sacrificial layer 12 and the second sacrificial layer 13 while maintaining the diameter of the cavity. In the case of this example, the cavity 5 with a height of 300 nm which is the total of the thickness (200 nm) of the first sacrificial layer and the thickness (100 nm) of the second sacrificial layer can be formed. The entire cavity 5 is formed, and then the second electrode 6 containing aluminum is formed on the membrane 9 (FIG. 3J). Then, finally, by depositing the silicon nitride film 10 with a PE-CVD device, the etching hole 8 which is made to open to remove the first sacrificial layer 12 and the second sacrificial layer 13 is sealed (FIG. 3K).

In this example, the height of the entire cavity 5 is 300 nm which is the total of the thickness of the first sacrificial layer 12 and the thickness of the second sacrificial layer 13. The diameter of the entire cavity 5 can be determined by the patterning of the second sacrificial layer 13. When producing the configuration having the cavity height of 300 nm by former production methods, a sacrificial layer having a height of 300 nm is formed beforehand, and then patterned into a cavity shape. Then, a membrane of a thickness which can sufficiently cover the height (sufficient coverage can be attained) needed to be formed thereon. Therefore, in order to cover the 300 nm high sacrificial layer, it is considered that a membrane having a thickness of at least 300 nm is required. However, according to the present production method, the thickness of the membrane 9 can be determined in accordance with the thickness (100 nm) of the second sacrificial layer 13 with respect to the 300 nm high cavity, and therefore it is sufficient that the thickness of the membrane is 150 nm. Therefore, also in the configuration in which the cavity height is large, the degree of freedom in the membrane thickness improves, so that the degree of freedom in design improves.

Example 2

Figure 4:
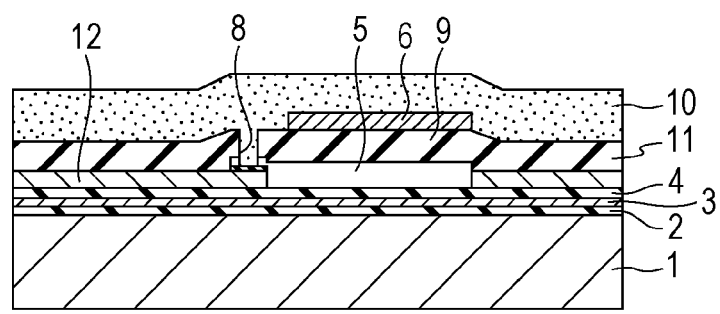
FIG. 4 is a cross sectional view of another example of the capacitive micromachined ultrasonic transducer according to an aspect of the present invention.

FIG. 4 shows Example 2 of the capacitive micromachined ultrasonic transducer according to an aspect of the present invention. A method for producing the capacitive micromachined ultrasonic transducer according to this example is described with reference to the process flow of FIGS. 5A to 5E, FIGS. 5F to 5I, and FIGS. 5J to 5L.

Figure 5A:
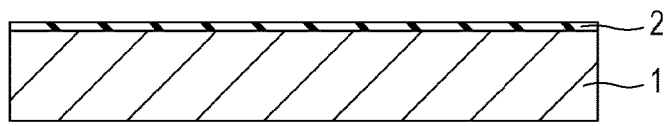
FIGS. 5A to 5E are cross sectional views of another example of the production method according to an aspect of the present invention.
Figure 5B:
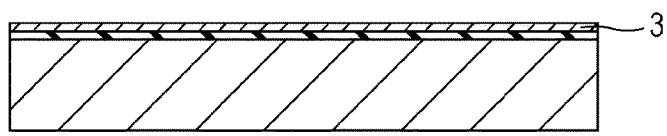
Figure 5C:
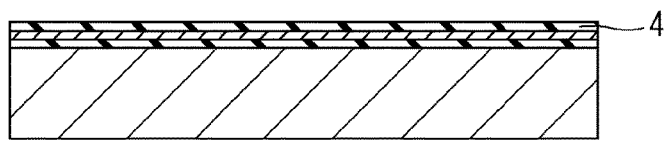
Figure 5D:
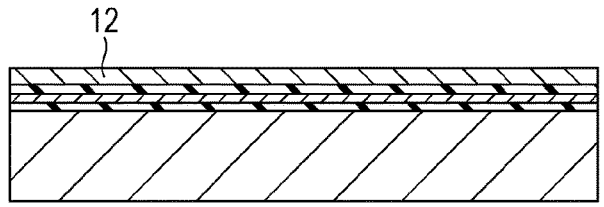
Figure 5E:
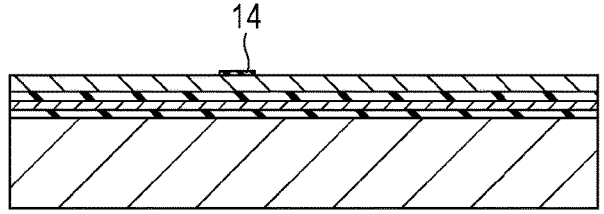
Figure 5F:
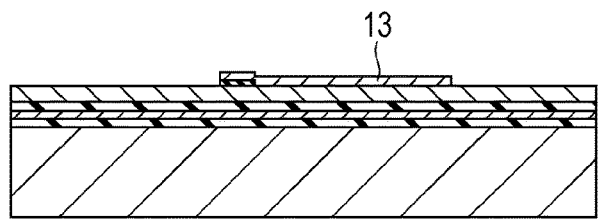
FIGS. 5F to 5I are cross sectional views of another example of the production method according to an aspect of the present invention.
Figure 5G:
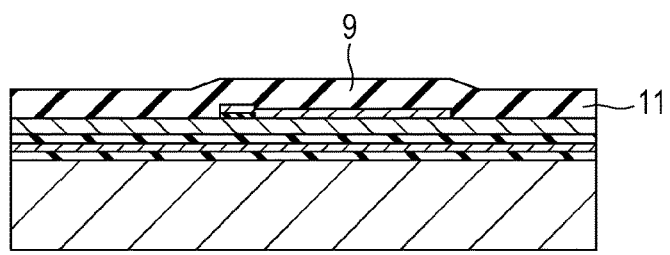
Figure 5H:
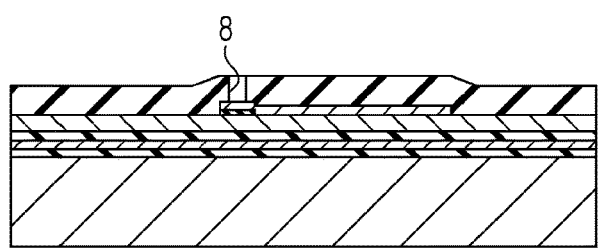
Figure 5I:
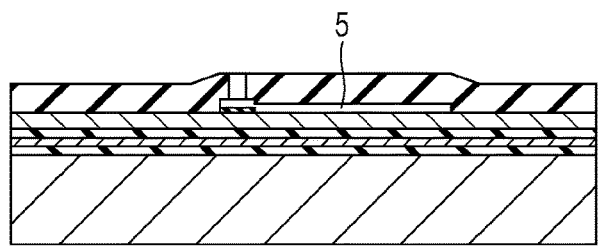
Figure 5J:
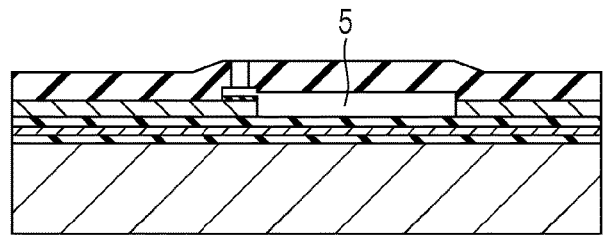
FIGS. 5J to 5L are cross sectional views of another example of the production method according to an aspect of the present invention.
Figure 5K:
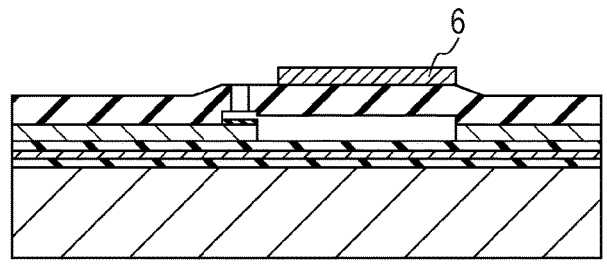
Figure 5L:
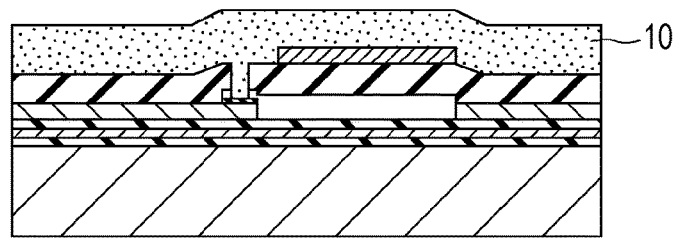

The production method in this example is not basically different from the production method of Example 1, and a configuration in which the cavity height is large is produced using a sacrificial layer containing two layers. However, when the cavity height is increased, the sealing film for sealing the etching hole which is used for etching the sacrificial layer needs to be increased. In this example, the insulating layer 2 of a thermal oxidation film is first formed on the silicon substrate 1, the first electrode 3 of tungsten is formed on the insulating layer 2, the insulating film 4 of a silicon oxide film is formed on the first electrode 3, and then an amorphous silicon which is the first sacrificial layer 12 is formed on the insulating film 4 (FIGS. 5A to 5E). Thereafter, the insulating film 14 containing a silicon nitride film is formed on a portion where the etching hole 8 is to be formed between the first sacrificial layer 12 and the second sacrificial layer 13 (FIG. 5E). Then, chromium which is the second sacrificial layer 13 and a silicon nitride film which is the membrane 9 are formed (FIGS. 5F to 5G), and then the second sacrificial layer 13 and the first sacrificial layer 12 are removed by sacrificial layer etching (FIGS. 5H to 5J). Then, the second electrode 6 is formed, and then the sealing film 10 is deposited on the etching hole 8 which is made to open in order to perform the sacrificial layer etching to seal the cavity (FIGS. 5K to 5L).

Since the silicon oxide film 14 is formed on the first sacrificial layer 12 in the portion of the etching hole 8 at this time, the first sacrificial layer 12 is not etched. Therefore, the height of the entire cavity 5 formed by performing the sacrificial layer etching is the total thickness of the first sacrificial layer 12 and the second sacrificial layer 13, and the height of the cavity in the portion of the etching hole 8 is set based on the thickness of the second sacrificial layer 13. Therefore, the thickness of the sealing film for sealing the cavity is determined based on thickness of the second sacrificial layer. Therefore, even in the case of a configuration in which the cavity height is large, the degree of freedom in the thickness of the membrane and the sealing film improves, so that the degree of freedom in design improves.

Another Embodiment

The transducer described above can be applied to a subject information acquisition device, such as an ultrasonic diagnosis apparatus. By receiving acoustic waves from a subject with the transducer and using electric signals to be output, a subject information reflecting optical characteristic values, such as an optical absorption coefficient, of the subject and a subject information reflecting a difference in acoustic impedances can be acquired.

More specifically, the information acquisition device irradiates a subject with light (electromagnetic waves including visible light, infrared rays, and the like) as an example. Thus, photoacoustic waves generated in a plurality of positions (portions) in the subject are received, and then a characteristic distribution which shows distribution of the characteristic information of each of the plurality of positions in the subject is acquired. The characteristic information acquired by the photoacoustic waves show the characteristic information relating to absorption of light and includes characteristic information reflecting the initial sound pressure of the photoacoustic waves produced by light irradiation, the light energy absorption density or absorption coefficient derived from the initial sound pressure, the concentration of substances configuring the organization, and the like. The substance concentration includes, for example, an oxygen saturation, a total hemoglobin concentration, an oxyhemoglobin or deoxyhemoglobin concentration, and the like. The information acquisition device can be used for diagnosis of malignant tumors, blood vessel diseases, and the like of human beings and animals, follow-up observation of chemical treatment, and the like. Therefore, a living body is assumed as the subject, specifically, diagnosis targets, such as a breast, a cervix, an abdomen, and the like of human beings and animals, are assumed. As an optical absorbent in the subject, an organization having a relatively high absorption coefficient in the subject is mentioned. For example, when a part of a human body is a subject, oxyhemoglobin or deoxyhemoglobin and blood vessels containing a large amount of oxyhemoglobin or deoxyhemoglobin, tumors containing a large number of new blood vessels, plaques on the carotid wall, and the like are mentioned. Furthermore, utilizing gold particles, graphite, and the like, a molecular probe specifically bonded to malignant tumors and the like, a capsule which delivers a pharmaceutical agent, and the like serve as the optical absorbent.

By receiving not only acoustic waves but reflected waves produced by an ultrasonic echo obtained by reflection of ultrasonic waves transmitted from a probe containing a transducer in a subject, a distribution of acoustic characteristics in a subject can also be acquired. The distribution of acoustic characteristics includes a distribution reflecting a difference in acoustic impedances of organizations in a subject.

Figure 6A:
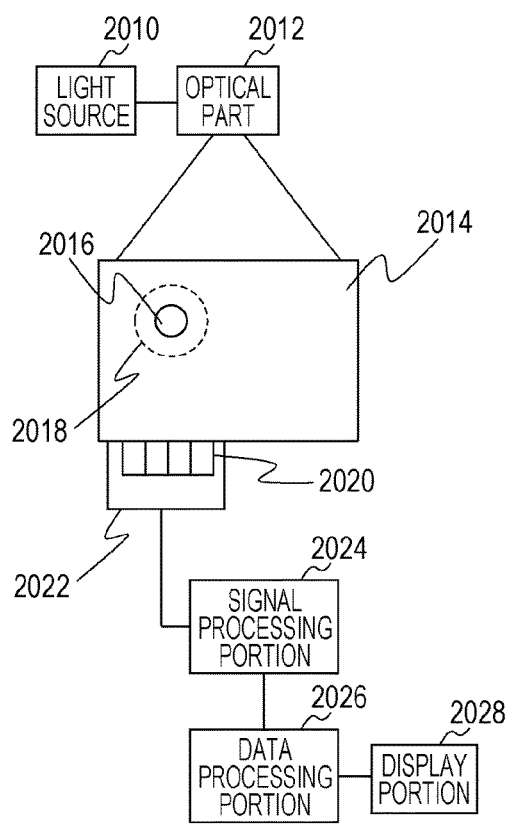
FIGS. 6A and 6B are entire block diagrams showing an example of an information acquisition device containing the transducer according to an aspect of the present invention.

FIG. 6A illustrates an information acquisition device utilizing a photoacoustic effect. A pulse light oscillated from a light source 2010 is emitted to a subject 2014 through an optical element 2012, such as a lens, a mirror, or an optical fiber. An optical absorbent 2016 present in the subject 2014 absorbs the energy of the pulse light to generate photoacoustic waves 2018 which are acoustic waves. A transducer 2020 according to an aspect of the present invention in a probe portion 2022 receives the photoacoustic waves 2018 to convert the same to electric signals, and then outputs the electric signals to a front end circuit of the probe portion. In the front end circuit, signal processing of a preamplifier and the like is performed, and then transmits the processed signals to a signal processing portion 2024 of a body portion through a connection portion. The signal processing portion 2024 performs signal processing, such as A/D conversion and amplification, of input electric signals, and then similarly outputs the processed signals to a data processing portion 2026 of the body portion. The data processing portion 2026 acquires subject information (characteristic information reflecting optical characteristic values, such as an optical absorption coefficient, of a subject) as image data using the input signals. Herein, the signal processing portion 2024 and the data processing portion 2026 are collectively referred to as a processing portion. A display portion 2028 displays an image based on image data input from the data processing portion 2026. A configuration in which the probe portion 2022 and the body portion are integrated can also be employed.

Figure 6B:
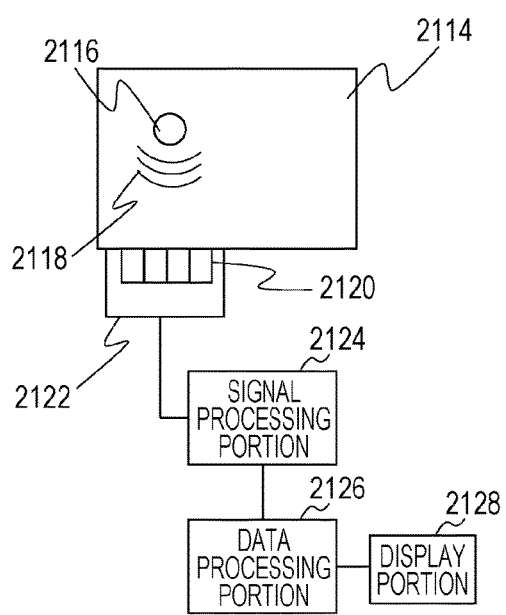

FIG. 6B illustrates an information acquisition device, such as an ultrasonic echo diagnosis apparatus utilizing reflection of acoustic waves. Acoustic waves transmitted from a transducer 2120 according to an aspect of the present invention in a probe portion 2122 to a subject 2114 are reflected by a reflector 2116. The transducer 2120 receives reflected acoustic waves (reflected waves) 2118, converts the reflected acoustic waves 2118 to electric signals, and then outputs the electric signals to a front end circuit in a probe portion. The front end circuit performs signal processing of a preamplifier and the like, and then transmits the processed signals to a signal processing portion 2124 of a body portion through a connection portion. The signal processing portion 2124 performs signal processing, such as A/D conversion and amplification, of the input electric signals, and then similarly outputs the processed signals to a data processing portion 2126 of the body portion. The data processing portion 2126 acquires subject information (characteristic information reflecting a difference in acoustic impedances) as image data using the input signals. Herein, the signal processing portion 2124 and the data processing portion 2126 are also collectively referred to as a processing portion. A display portion 2128 displays an image based on the image data input from the data processing portion 2126. Herein, a configuration in which the probe portion 2122 and the body portion are integrated can also be employed.

The probe portion is one which performs mechanical scanning and may be one which is moved to a subject by users, such as a doctor and an engineer (handheld type). In the case of a device using reflected waves as illustrated in FIG. 6B, a probe of transmitting acoustic waves may be provided separately from a probe of receiving the same. Furthermore, an apparatus having both the functions of the devices of FIG. 6A and FIG. 6B may be configured to acquire both the subject information reflecting the optical characteristic values of a subject and the subject information reflecting the difference in acoustic impedances. In this case, the transducer 2020 of FIG. 6A may be configured to not only receive photoacoustic waves but transmit acoustic waves and receive reflected waves.

According to the present invention, even when the height of a cavity is large, the thickness of a vibration membrane can be relatively flexibly set, so that the degree of freedom in design of cell structures can be increased.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-125834, filed Jun. 18, 2014, which is hereby incorporated by reference herein in its entirety.

What is claimed is:

1. A method for producing a capacitive micromachined ultrasonic transducer, having a cell structure, the cell structure comprising a first electrode and a vibration membrane containing a second electrode, the vibration membrane provided with a cavity interposed between the first electrode and the second electrode, the method comprising:
   forming the first electrode;
   forming a first sacrificial layer on the first electrode;
   forming a second sacrificial layer on a portion corresponding to a part of the cavity on the first sacrificial layer;
   forming an insulating layer configuring at least a part of the vibration membrane on the second sacrificial layer;
   removing the second sacrificial layer by etching through an opening formed in the insulating layer; and
   after the second sacrificial layer is removed, removing a part of the first sacrificial layer and leaving other part of the first sacrificial layer.

2. The method according to claim 1, further comprising sealing the opening.

3. The method according to claim 1, wherein a material of the first sacrificial layer comprises silicon and a material of the insulating layer comprises a silicon nitride film or a silicon oxide film.

4. The method according to claim 1, wherein a material of the first sacrificial layer comprises amorphous silicon, a material of the second sacrificial layer comprises chromium, a material of the first electrode comprises aluminum, and a chromium etching solution containing ceric ammonium nitrate and nitric acid is used as an etchant for the second sacrificial layer.

5. The method according to claim 1, wherein a material of the first sacrificial layer comprises amorphous silicon, a material of the first electrode comprises aluminum, and gas containing $XeF_2$ is used as an etchant for the first sacrificial layer.

6. The method according to claim 1, wherein the first sacrificial layer is formed on the first electrode through an insulating layer.

7. The method according to claim 1, wherein the insulating layer is formed on a part of the first sacrificial layer, and then the second sacrificial layer is formed.

8. The method according to claim 7, wherein the opening is formed on the insulating layer.

9. The method according to claim 1, wherein materials of the first sacrificial layer and the second sacrificial layer comprises different material from each other.

10. A capacitive micromachined ultrasonic transducer, having a cell structure, the cell structure comprising a first electrode and a vibration membrane containing a second electrode, the vibration membrane provided with a cavity interposed between the first electrode and the second electrode, wherein a support portion, which supports the vibration membrane of the cell in such a manner as to be able to vibrate, is provided, and the support portion includes a sacrificial layer left behind when forming the cavity by sacrificial layer etching, wherein a part of the sacrificial layer left behind is provided closer to the first electrode than a sealing portion in an etching hole used for etching the sacrificial layer.

11. A subject information acquisition device comprising:
the capacitive micromachined ultrasonic transducer according to claim 10; and
a processing portion configured to acquire and process information of a subject using an electric signal output from the capacitive micromachined ultrasonic transducer, wherein
the capacitive micromachined ultrasonic transducer receives an acoustic wave from the subject and outputs an electric signal.

12. The subject information acquisition device according to claim 11, further comprising:
a light source,
wherein the capacitive micromachined ultrasonic transducer receives an acoustic wave generated when an electromagnetic wave oscillated from the light source is emitted to the subject, and then converts the acoustic wave to an electric signal.

13. The capacitive micromachined ultrasonic transducer according to claim 10 wherein a material of the sacrificial layer left behind comprises amorphous silicon.

14. A capacitive micromachined ultrasonic transducer having a cell structure, the cell structure comprising a first electrode and a vibration membrane containing a second electrode, the vibration membrane provided with a cavity interposed between the first electrode and the second electrode, wherein
a support portion, which supports the vibration membrane of the cell in such a manner that the vibration membrane is able to vibrate, is provided between the first electrode and the vibration membrane,
the support portion includes a layer containing at least amorphous silicon, and
the layer containing amorphous silicon is provided between the first electrode a sealing portion provided on the vibration membrane to seal the cavity.

15. The capacitive micromachined ultrasonic transducer according to claim 10, wherein a shape of the vibration membrane is one of a circular shape, a rectangular shape, and a hexagonal shape.

16. The capacitive micromachined ultrasonic transducer according to claim 10, wherein an insulation film is provided between the first electrode and the cavity.

17. The capacitive micromachined ultrasonic transducer according to claim 14, wherein the vibration membrane includes a silicon oxide film, or a silicon nitride film.

18. The capacitive micromachined ultrasonic transducer according to claim 10, wherein the vibration membrane includes a silicon nitride film.

19. The capacitive micromachined ultrasonic transducer according to claim 10, wherein the first electrode contains one of titanium, aluminum, molybdenum, and tungsten.

20. The capacitive micromachined ultrasonic transducer according to claim 10, wherein the second electrode contains titanium, or aluminum.

* * * * *